(12) United States Patent
Walsh et al.

(10) Patent No.: US 6,655,583 B2
(45) Date of Patent: Dec. 2, 2003

(54) MEDICAL BILLING METHOD AND SYSTEM

(75) Inventors: Christopher S. Walsh, Fredericksburg, VA (US); Robert Joseph Crowder, Jr., Fredericksburg, VA (US)

(73) Assignee: Advanced Medical Interventions, Inc., Fredericksburg, VA (US)

( * ) Notice: Subject to any disclaimer, the term of this patent is extended or adjusted under 35 U.S.C. 154(b) by 0 days.

(21) Appl. No.: 10/140,215

(22) Filed: May 8, 2002

(65) Prior Publication Data

US 2002/0148893 A1 Oct. 17, 2002

Related U.S. Application Data

(63) Continuation-in-part of application No. 09/833,785, filed on Apr. 13, 2001, now Pat. No. 6,464,136.

(51) Int. Cl.[7] .................................................. G06K 5/00
(52) U.S. Cl. .................. 235/380; 235/375; 235/477.01; 235/383; 705/3; 705/2; 705/1; 705/41; 705/38
(58) Field of Search ................................ 235/380, 375, 235/472.01, 383; 705/3, 2, 1, 41, 38

(56) References Cited

U.S. PATENT DOCUMENTS

| | | | |
|---|---|---|---|
| 4,857,716 A | * | 8/1989 | Gombrich et al. .......... 235/375 |
| 5,510,606 A | * | 4/1996 | Worthington et al. .. 235/462.46 |
| 5,672,154 A | * | 9/1997 | Sillen et al. ................. 604/503 |
| 5,772,585 A | * | 6/1998 | Lavin et al. ................. 600/300 |
| 5,822,544 A | * | 10/1998 | Chaco et al. .................. 705/2 |
| 5,842,976 A | * | 12/1998 | Williamson ................. 600/300 |
| 6,222,452 B1 | * | 4/2001 | Ahlstrom et al. ........ 340/572.1 |
| 6,305,605 B1 | * | 10/2001 | Goetz et al. ................ 235/385 |
| 6,342,839 B1 | * | 1/2002 | Curkendall et al. ...... 340/573.3 |

* cited by examiner

Primary Examiner—Karl D. Frech
Assistant Examiner—Allyson Sanders
(74) Attorney, Agent, or Firm—Larson & Taylor, PLC

(57) ABSTRACT

A billing method is provided for billing for medical treatments and other services. The method includes capturing a treatment event by electronically scanning, at the time of the treatment event, a machine readable patient identifier (e.g., a bar code) carried by a patient treatment chart. The chart has entered thereon a prescribed treatment schedule. Capture of treatment event is entered into a computerized billing system along with the corresponding patient identifier. The patient treatment chart is used to validate charges entered into the system. All treatment events that are entered into the billing system for a particular patient identifier are collected and an invoice is generated for all of the collected treatment events entered into the billing system for the specific patient identifier. A method is also provided for tracking the patient treatment chart as an alerting device in checking on charge capture.

38 Claims, 4 Drawing Sheets

MEDICAL BILLING METHOD AND SYSTEM

CROSS REFERENCE TO RELATED APPLICATIONS

This application is a Continuation-In-Part of application Ser. No. 09/833,785 filed on Apr. 13, 2001 now U.S. Pat. No. 6,464,136.

FIELD OF THE INVENTION

The present invention relates to billing methods and systems, and, more particularly but not exclusively, to billing methods and systems for capturing and billing medical services and disbursements.

BACKGROUND OF THE INVENTION

Although, as indicated above, the present invention is not limited to such an application, the invention is of particular advantage in billing medical services and related charges. Further, the invention is particularly useful in billing medical services associated with the treatment of cancer, i.e., radiation treatments and the like.

With any billing system it is important to capture billing events, i.e., the dispensing of services rendered that are properly billable to the patient. In a cancer treatment setting, these events can include such services as patient consultation, treatment planning, simulations, dosimetry, devices, port verification, daily treatments, special dosimetry, special teleport, plans (identified by the code number 77321) and special Trx procedures (identified as 77470), ultrasound guided radiation treatment delivery and the like.

Conventional cancer billing typically involve the use of a record and verify system reports and/or the manual collection of charges from treatment documentation in order to create a "superbill" which includes all patient charges for a given treatment session or time period. The superbill is then used to input the charges into the billing system in a batch billing process to produce the invoices that are sent to both the insurance companies and the patients. One major disadvantage of such a system or approach is that record and verify systems are typically associated with equipment use (e.g., the use of the accelerator for radiation treatments) and the system does not capture all of the services for which the facility or doctor can legitimately bill.

More generally, record and verify systems are designed to capture billing for hospital/technical (diagnostic professional/technical) transactions, but there are many other process-based procedures performed that are billable by both the facility and the physician outside of these captured transactions. For example, IMRT (Intensity Modulated Radiation Therapy) can be considered to be a process-based procedure.

A further problem is that physicians are mandated by the Office of the Inspector General (OIG) to take responsibility for their charges and thus any billing system must ensure that only legitimate charges are billed and that these charges are accurately reflected in the corresponding billing statements. Batch billing, i.e., a billing system wherein all billing information for, e.g., a given month is collected together at the end of the month and then billed out at that time, is inefficient, and essentially inappropriate, for radiation oncology because of the shift in the field away from a transaction-based approach to a setting featuring (i) process-based patient care and (ii) serious insurance filing time constraints. In the latter regard, problems occur in filing insurance claims on time simply because batch billing is not real time billing. Further, as will appear, the standard requirements of insurance companies as to when successive treatments can be billed out result in further constraints on any billing system.

SUMMARY OF THE INVENTION

In accordance with the invention, a medical billing method and system are provided which overcome important disadvantages of medical billing systems currently in use. Although, as indicated above, the invention is not limited to such an application, the invention is particularly useful in billing for radiation treatments and associated procedures, medications and treatment accessories and equipment. The method of the invention provides an independent, automated approach to the capture of treatment events (e.g., individual radiation treatments). The invention results in efficient, complete accurate billing and documentation of charges (e.g., the charges of an oncology facility and physician) in real time and can be used in basically any treatment setting (e.g., with any radiation treatment unit). The independent charge capture provided helps ensure that payment is received for all properly billable services (e.g., all radiation oncology services) because accurate charge capture leads to accurate billing, resulting in faster payments, to prompt responses to erroneous insurance denials and, ultimately, to substantially higher collected revenue.

In accordance with one aspect of the invention, there is provided a billing method for billing for medical treatments, the method comprising: capturing a treatment event by electronically scanning, at the time of the treatment event, a machine readable patient identifier carried by a patient treatment chart having entered thereon a prescribed treatment; entering the captured treatment event into a computerized billing system along with the corresponding patient identifier; using said patient treatment chart to validate charges entered into computerized billing system; collecting all treatment events that are entered into the billing system; and generating an invoice for all of the collected treatment events entered into the billing system for the specific patient identifier.

Preferably, the patient treatment chart contains a prescribed schedule of treatments for the patient. Advantageously, in capturing a treatment event, an indication is provided as to whether or not a specific treatment of the prescribed schedule of treatments has been carried out. In an advantageous implementation, a dialog box is presented to a system user on a monitor located at the site at which the treatment event takes place; the dialog box presents choices corresponding to (i) full treatment, (ii) partial treatment and (iii) no treatment, and the user checks the appropriate box to indicate the treatment, if any, that was performed.

In a very important embodiment, the treatment event is entered into the treatment chart at the time the treatment takes place. It is much preferred that the treatment chart be updated in real-time as treatment events take place because the chart is the documentation used to validate charges being billed. In one preferred implementation, an independent treatment event capture system is used to inform the billing personnel when specific patients have reached a billable "milestone" as described below. However, even with the generation of a corresponding milestone report, the patient chart should be used to verify that the charges are appropriate before entering them into the billing system. Thus, even with a charge capture system, the patient chart should be used as a final verification mechanism.

Preferably, as indicated above, a milestone billing report is generated after a predetermined number of the treatment events is captured, and generation of a patient bill by the billing system takes place responsive to the generation of the milestone report. In an implementation tailored to current insurance practices in the United States, the billing system designates every fifth treatment event as a milestone for triggering generation of the milestone billing report. Preferably, the milestone billing report includes the patient name, milestone information, and bill date information for a given milestone, the bill date being the date of the first treatment of the milestone. Advantageously, when a full course of treatment for the patient is completed and the number of leftover unbilled treatments is not divisible by five, the billing system, in billing for the leftover treatments, treats the leftover treatments as a further milestone should there be three or more unbilled treatments, and again assigns the bill date as the date of the first treatment of the milestone. In an advantageous implementation, the billing system enables a user to log on to check whether the milestones are being properly reported. Preferably, this check is made by the billing system when a milestone is generated to check whether the milestones are being properly reported. Advantageously, this check is made to check for at least one of the following errors: (i) items on the patient chart are not billed out and (ii) a prescribed treatment schedule is not entered into the chart.

Preferably, the billing system provides that, in generating the patient bill, nothing can be billed for that is not entered into the patient treatment chart.

According to a further aspect of the invention, there is provided a billing method for billing for medical treatments administered to a patient, the method comprising: capturing an independent treatment event by electronically scanning, at the time of the treatment event, a machine readable patient identifier for identifying the patient; entering, at the time of the treatment event, data with respect to the treatment event and other billable items, into a patient treatment chart associated with the specific patient identifier; monitoring the treatment events captured for each specific patient identifier and, when the number of treatment events for a specific patient identifier reaches a predetermined number, selecting the patient treatment chart associated with the specific patient identifier; and when the treatment chart is selected, generating an invoice identified by the patient identifier based on the patient treatment chart.

Preferably, the machine readable identifier is carried by the patient treatment chart and the patient treatment chart has entered thereon a prescribed schedule of treatment events.

Advantageously, the method further comprises electronically scanning a corresponding machine readable patient identifier associated with an element employed in connection with the treatment event. When the method is used in connection with radiation therapy, the element preferably comprises a port film and/or a diode.

Preferably, as indicated above, the method further comprises providing an indication whether or not a specific treatment of the prescribed schedule of treatments has been carried out and this is advantageously done using the monitor presentation described previously.

Advantageously, a milestone billing report is generated each time the number of treatment events reaches a milestone of a fifth successive treatment in a series of treatments of a patient. As described above, in a preferred implementation, the milestone billing report includes the patient name, milestone and information bill date information for a given milestone date, the bill date being the date of the first treatment of the milestone.

In accordance with yet another aspect of the invention, there is provided a method of facilitating billing for medical treatment services involving treatment of a patient wherein a patient treatment chart is used in conjunction with the treatment of the patient, the method comprising the steps of: logging onto a computerized billing system when the patient treatment chart is located at a predetermined location in a treatment facility; and generating a billing alert in response to said logging on step so as to ensure patient treatment provided at said location will be billed out.

Preferably, the logging on step comprises logging on responsive to use of a scanning device located at the predetermined location to scan a patient identifier on the patient treatment chart.

Further features and advantages of the present invention will be set forth in, or apparent from, the detailed description of preferred embodiments thereof which follows.

DESCRIPTION OF THE PREFERRED EMBODIMENTS

Figure 1:
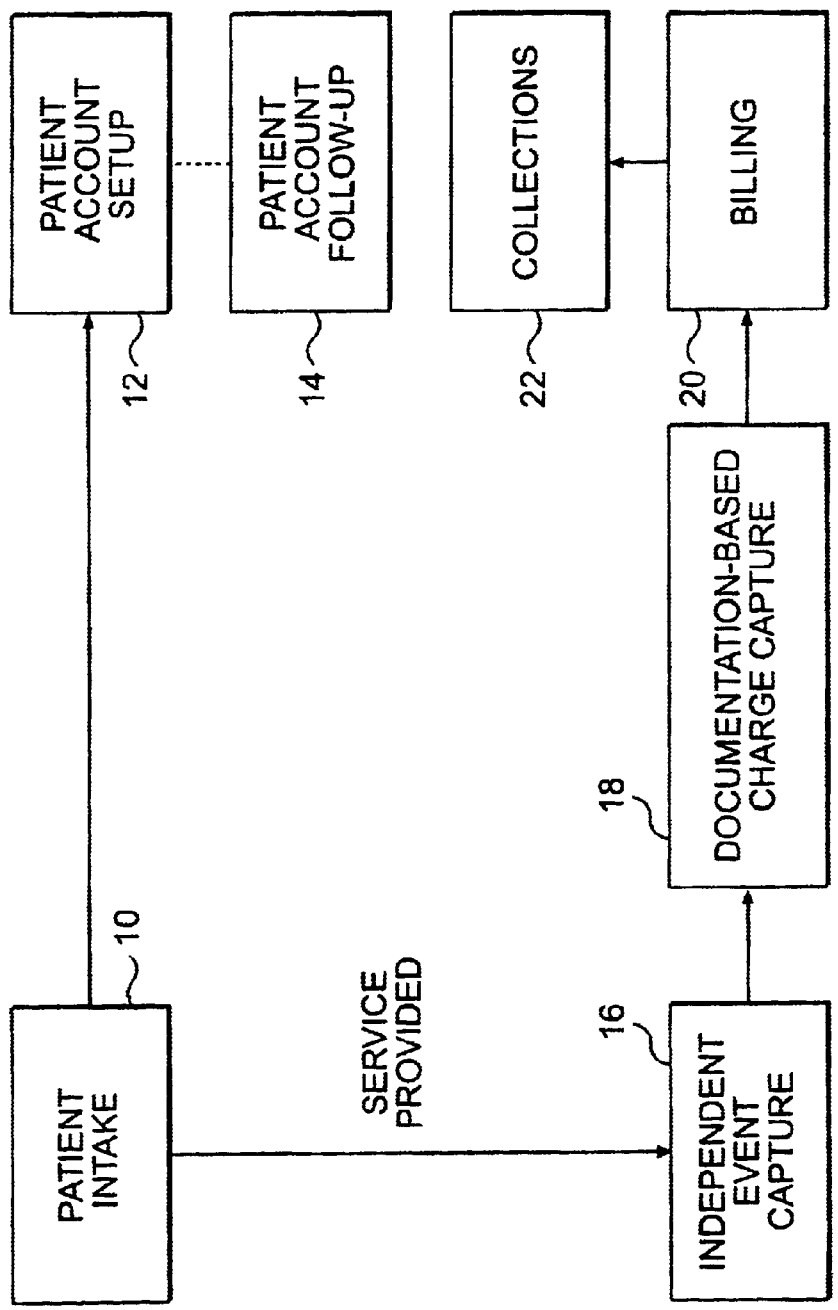
FIG. 1 is a block diagram/flowchart of the basic, overall billing method and system of the invention.

Before considering some of the important features of the billing method or system of the invention, a brief overview will be provided of the overall method or system. Referring to FIG. 1, the billing process begins with patient intake, as indicated by block 10, and, as described in more detail below, this involves gathering information about the patient, including, e.g., insurance information. This leads to setup of a patient account, block 12, and later in the process after patient services have been rendered, a patient account follow-up, block 14.

After a service is provided at the particular cancer center or other treatment facility, a process referred to as independent event capture is effected, as indicated by block 16. This process is, again, described in more detail below. In a preferred embodiment, this process employs techniques described in my co-pending application Ser. No. 09/473,638, filed on Dec. 28, 1999, and Ser. No. 09/833,785, filed on Apr. 13, 2001. Independent event capture leads to a documentation-based charge capture, block 18, on which billing, block 20, and, ultimately, collections, block 22, are based.

Figure 2:
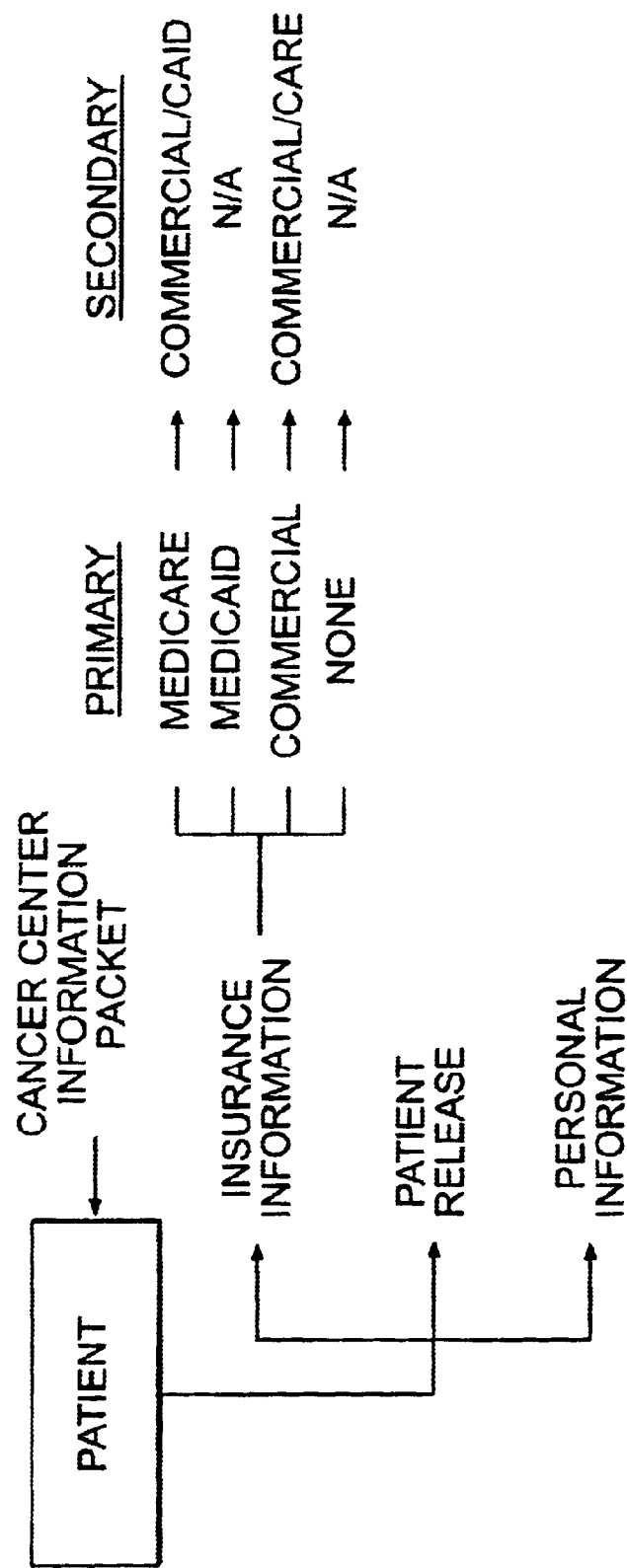
FIG. 2 is a block diagram/flowchart of the patient intake procedure of FIG. 1.

Considering in more detail the patient intake process represented by block 10 in FIG. 1 and referring now to FIG. 2, at the time patient is referred to a cancer center, the center determines the need for a referral or authorization as an appointment is arranged to see a treating physician or other treatment personnel. The center staff then secures the appropriate referrals or authorizations and the patient is scheduled for consultation. As is also indicated in FIG. 2, the patient is preferably provided with a radiation oncology billing information packet that includes policies on insurance billing, payment and collections. As indicated, this results in the generation of insurance information on both the primary insurer (e.g., as shown, Medicare, Medicaid, commercial or none) and the secondary insurer (where applicable), as well as a patient release and whatever personal patient information is required.

Figure 3:
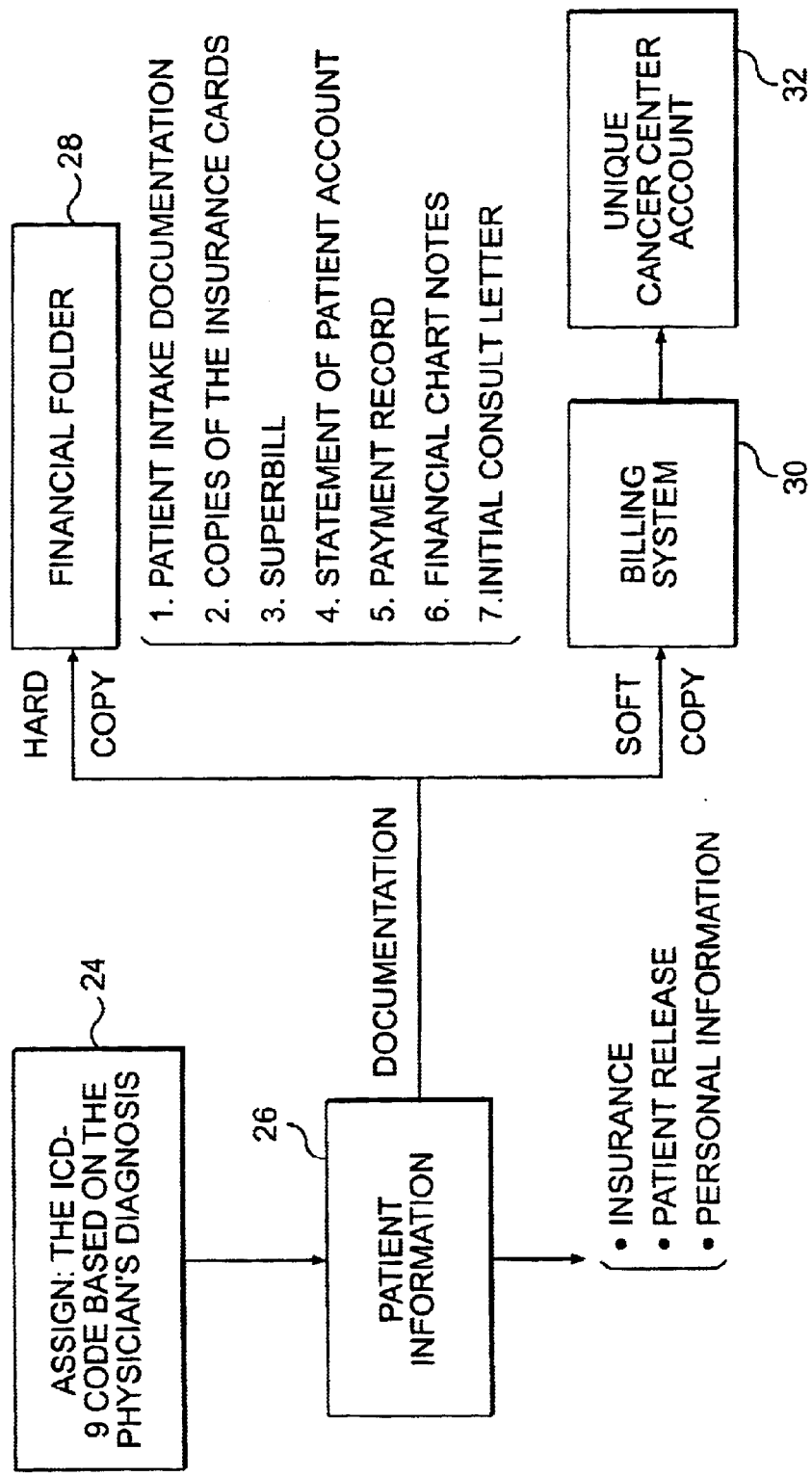
FIG. 3 is a block diagram/flowchart of the patient account setup and documentation procedures of FIG. 1.

The patient account setup represented by block 12 in FIG. 1 will now be considered in connection with FIG. 3. As part of this setup, as indicated by block 24, the system assigns the appropriate ICD-9 code based on the physician's diagnosis. An ICD-9 code is a standard code which is used to identify different diagnoses. For example, the ICD-9 diagnosis code for prostate cancer is 185. As indicated in FIG. 3, this information, together with other patient information, indicated by block 26 (and including, e.g., insurance, patient release, personal information and the like) is documented in both hard copy and soft copy form. The hard copy is placed in a financial folder, block 28, which, as indicated, may include, ultimately, patient intake documentation, copies of insurance cards, a superbill, a statement of patient account, a payment record, financial chart notes, the initial consultation letter, and the like. The soft copy goes to the billing system, block 30, and from thence to a unique cancer center account, block 32. The information obtained during this phase is the basis for an efficient and accurate billing approach that results in timely payments.

Turning now to the independent event capture step in the overall process (block 16 in FIG. 1), as indicated above, in accordance with a preferred embodiment, this process employs the methods described in pending U.S. application Ser. No. 09/473,638, filed on Dec. 28, 1999, and Ser. No. 09/833,785, filed on Apr. 13, 2001, the disclosures of which are hereby incorporated by reference. In one specific embodiment, involving radiation treatment using a linear accelerator, a verification work station, preferably including a computer and monitor, a magnetic code reader, a bar code reader and a speaker, is provided in the treatment room, while a corresponding accelerator work station and associated monitor are located in a treatment console area. In general, the method disclosed in these patent applications requires, inter alia, reading of a patient identifier, e.g., a bar code, carried by a patient chart as part of a patient identification process (as well as to gain access to the accelerator), thereby ensuring that the patient chart is brought into the treatment room. Further, a cross checking process ensures that the prescribed treatment indicated by the chart is carried out. Thus, the treatment chart is used to capture the treatment events surrounding the use of the accelerator.

Although the use of a hard copy of the treatment chart is preferred, in an alternative embodiment an electronic medical record can be used and a separate patient identifier can be employed, e.g., on a "smart" card which stores the electronic medical record.

As discussed in application Ser. No. 09/833,785, one important aspect of the invention concerns the provision of a method and system which are specifically designed to ensure capture of charges that are sometimes missed in billing for medical services. In general, the system requires for logging in, at a verification station or other monitor, the presence of a patient treatment chart or check sheet at a particular location, such as at a treatment room as described above. The presence of the chart at the location in question (e.g., the treatment room) can be determined based on an event involving the chart, such as scanning of the chart at that location by a scanning device (e.g., the bar code reader mentioned above), or by using a passive tracking system wherein a transmitter is placed on the chart and the location thereof is determined by receivers designed to keep track of the locations of the documents being monitored. When the patient treatment chart is in the room, the presumption by the system is that the patient is being treated and thus that services are being rendered that should be billed for. By logging in the presence of the chart at the treatment system, the billing system is alerted to the fact that treatment has occurred or will occur and that a bill for that treatment should be generated. If no bill is generated, a query is triggered by the billing system and an inquiry is made. This aspect of the invention should be of less importance with a billing system that employs the cross checking methods to which reference was made above but, at a minimum, serves as a check that helps assure that a particular treatment is billed out.

Although the inventions disclosed in the above-identified applications are not limited to this implementation, in a preferred embodiment disclosed in these applications, the audio signal is a short series of tones or a short bar or portion of music that is assigned to the patient and can be identified by the patient when the audio signal is generated in response, e.g., to reading of a bar code on a patient chart.

In accordance with a further aspect of the present invention, a further audio signal is generated, after the playing of the initial patient specific signal, which continues during treatment until the attending treatment personnel log off the associated computer system. The further audio signal would also be assigned to the patient and in an advantageous embodiment, the initial audio signal and the further audio signal would be related. For example, the further signal could be a song or other pleasing and/or soothing piece of music and the initial signal could be a short excerpt from (or some other part of) the song or other music. The further signal would loop, i.e., play on a continuous basis, until log off occurred. The patient would know his or her music and would be told not to get off of the treatment table until the further audio signal (e.g., song) was over. Before log off could occur, it would be necessary for the attending treatment personnel to enter all charges for treatments for the patient that had been carried out and to perform whatever final checks that were required. The treatment personnel will be motivated to promptly complete the treatment procedure, including all charge capture, so as to be able to log off and thus to free up the treatment room for the next patient. In this way, this aspect of the invention ensures, with the help of the patient, that all treatment charges are captured and that treatment is properly terminated.

Figure 4:
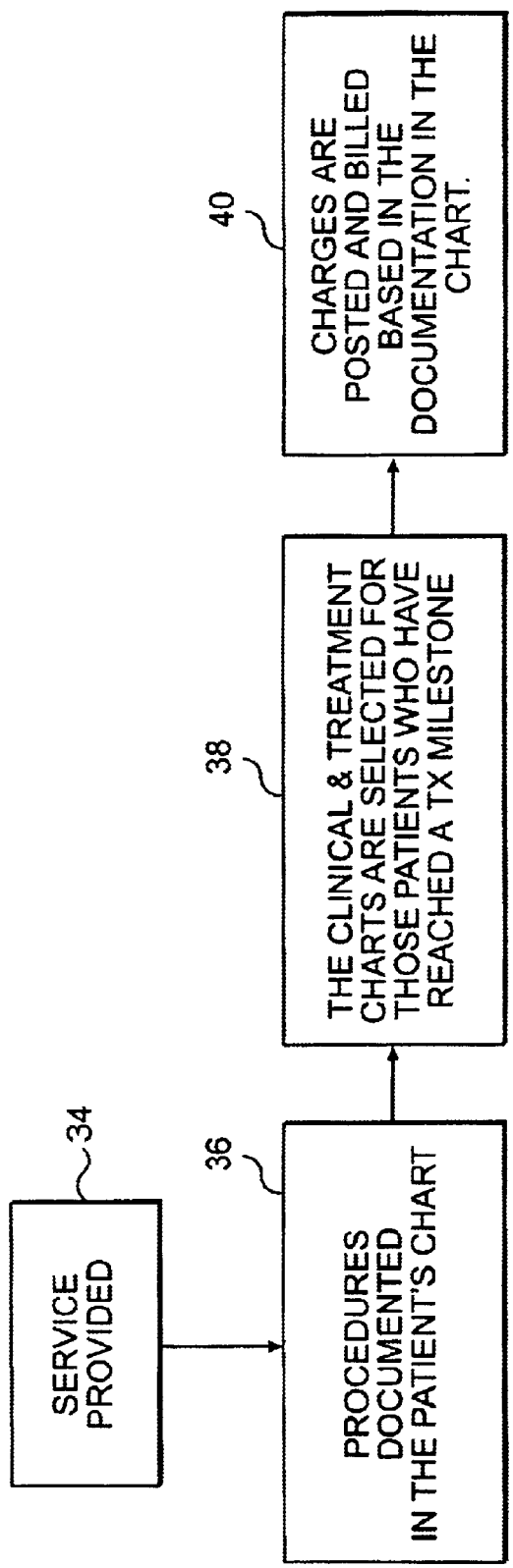
FIG. 4 is a block diagram/flowchart of key elements of the basic billing method and system of the invention.

The document-based billing (charge capture) step or approach indicated by block 18 in FIG. 1 will now be considered in more detail in connection with FIG. 4. As indicated therein, after a patient service has been rendered, block 34, and the procedures have been documented in the patient's treatment chart, the billing system selects the clinical and treatment charts for those patients who have reached a threshold or milestone with respect to number of treatments. In accordance with a further important aspect of the invention, the billing system generates a milestone report which serves as an independent queuing mechanism that supports the documentation based billing (e.g., in the exemplary case under consideration, radiation oncology documentation). The charges are then posted and billed based on the documentation contained in the chart, as indicated by block 40. Such document-based billing provides a proactive recovery mechanism for the charges which are inevitably missed, thereby substantially reducing the risk of charge omissions and of erroneous charge capture.

Considering the milestone system in more detail, as discussed above, an important feature of the invention is that it does away with the use of batch billing and provides a billing cycle as close to real time billing as is practical. A serious constraint on such billing is that posed by the medical billing requirements or procedures of medical insurance companies. For example, while there are many radiation oncology charges that can be billed in real time as they occur, there is one charge that the physician is required to bill as a group of five, viz., the weekly treatment, i.e., the weekly treatment charge. This weekly treatment charge is typically the largest single chargeable code for the physician (i.e., largest in terms of the amount of relative value units involved). The present invention uses this weekly treatment event as the sentinel audit mechanism for billing the charges that have occurred since the last weekly treatment charge. A further constraint is that when treatment is completed for a patient, at least three treatments must have been carried out before the treatments can be billed for, i.e., if only two further treatments have been carried out, these "dangling" treatments cannot be billed out.

In accordance with this aspect of the invention, the billing system designates every fifth treatment (e.g., the 5th, 10th, 15th, etc.) as a milestone. The milestone report to which reference was made above includes the patient name, milestone information and the weekly management bill date for the given milestone. The bill date is the milestone treatment date minus four prior treatment dates on which the patient was treated. Stated differently, the bill date is simply the first of the five treatment dates. Thus, if, as is the normal procedure for certain cancer patients, the treatments take place five days a week on Monday through Friday and the milestone date is a Friday, the weekly management bill date will be the Monday of that week. Accordingly, even though the medical billing procedures to which reference was made above do not permit billing on that Monday (because the set of five treatments is not complete), the billing system treats Monday as the bill date.

In a situation where a patient has undergone a total number of treatments not divisible by five (e.g., 38 treatments out of a planned 40 treatments), then the last week of treatment management comprises less than five treatments (38 minus 35 or three treatments in the example). As a consequence, three or more "dangling" treatments may be billed out during a particular weekly management period. At billing close out, the final weekly management bill date will be the date of the first "dangling" treatment that can be billed for (e.g., the first of three leftover treatments). It will be understood that these last few treatments in a given course of radiation therapy are often the most critical in determining whether a patient has been cured of the disease being treated without sustaining radiation complications.

It will be understood that the billing report is also applicable to a situation wherein a particular patient is being treated twice a day. Treating of a patient twice a day, rather than once a day, does not affect the system logic, but would merely result in a patient reaching a milestone every two and one-half days. In other words, for patients receiving two treatments per day (typically four hours apart), two weeks of management, and two reports, are generated for each five day week.

The treatment plan or schedule is also entered into the system so that when a treatment is carried out, account can be taken of the treatment actually administered. For example, a dialog box is preferably provided which includes the following choices: (1) full; (2) partial; and (3) none. Thus, when the treatment is given or is withheld for some reason, the proper box is checked, and the billing system knows what was done.

With the billing system just described, at a milestone (e.g., after the fifth treatment in a treatment plan), the system prints out a milestone report indicating that the billing cycle is to begin. Further, the user can log on to the system to make certain that all milestones are being properly reported. For example, if a milestone is generated but the chart items are not billed out or the treatment schedule is not entered, an inquiry is made.

In addition to scanning a patient treatment chart, an electronic sheet (e-sheet) or even an electronic medical record as mentioned above, billable events can be captured by scanning elements or devices associated with the event which carry, or have associated therewith (e.g., on a container), the machine readable patient identifier. For example, in connection with radiation therapy procedures, these elements can be a port film, i.e., a film, taken inside the treatment room, of the treated area, or a diode, i.e., a measurement device for measuring the radiation dose passing through the patient.

Because one of the key concerns of the billing system of the invention is to ensure to the extent possible that everything being billed is fully documented and to prevent billing for things that should not be billed for, in one preferred embodiment, the event capture system provides that after the chart has been scanned, scanning of, e.g., the diode cannot take place until a predetermined period has passed and/or other scans have been completed such as scanning of both a patient photograph and a check sheet.

It will be appreciated from the foregoing that event capture, review of the treatment schedule, and the documentation provided by the patient treatment chart or clinical chart provide the basic billing mechanism. To ensure that the system provides the necessary backup or documentation for every charge and to thus avoid mistaken charges, the system provides that nothing can be billed for that is not entered on the patient treatment chart.

The foregoing information goes to a billing computer which is preferably located at a dedicated facility apart from the treatment or at the treatment center itself. The captured charges are billed out electronically or an invoice is printed out and mailed. As indicated above, a superbill is generated which is hand keyed using the CPT codes that can be billed. (CPT is a registered trademark of the American Medical Association.) CPT codes are assigned numeric codes used in describing physician services. These codes are important because insurance payments are made based on these codes. In an advantageous implementation, patient statements are mailed out to all active patients on a monthly basis, with the balance on the patient's account being identified as either "patient due" or "insurance pending."

According to a further feature of the invention, the system produces a template of potentially billable CPT codes based on the matching of the ICD-9 evaluations to the CPT codes. This template would be used by the billing system as a check list for potentially billable procedures. Alternatively, or in addition, a patient's chart or other identifier can be scanned to provide an indication of potentially billable procedures associated with the patient's proposed treatment plan. These procedures change and for example, a hormone treatment may be added to the basic plan and this would be reflected in a chart change. Of course, a cornerstone of the billing method and system of the invention is that no procedures are billed for that are not documented. Thus, the template is merely an auditing guide and in no circumstance would be used directly to generate an actual bill or invoice.

In another approach to capturing potential charges normally associated with a particular procedure, sidebar boxes can be provided on the workstation monitor for the event capture system which would list the potentially billable items. In the example under consideration, the listings might normally include PVF (port verification film), diode, U/S (ultrasound) and IMRT.

As indicated above, in one preferred embodiment, the preferred embodiment, the event capture system, which is preferably based on the system described in the abovementioned Ser. Nos. 09/473,138 and 09/833,785, and is identified commercially as the VEEBAAT™ system, and the computerized billing system are separate systems. In this regard, the basic computerized billing system can be a commercially available system (such as Medical Manager™). Moreover, in this embodiment, the event capture system is located at the medical facility, preferably in the treatment room, while the billing system is located at a central billing office which services many different event capture systems.

With an arrangement such as just described, it is desired to perform checks on the data between the event capture system and the billing system to verify the data is kept synchronized (i.e., all events captured by the event capture system are appropriated recorded in the billing system for reimbursement). This could be accomplished in the following manner: each morning (for example) at the billing office, the billing manager would: (a) remotely log into the event capture system for each billing client via a modem; (b) remotely run, via the modem, the event capture program at each event capture site, generate a weekly treatment milestone report, and print the report; and (c) for each milestone listed, verify that the weekly treatment charge (preferably identified by a specific code) is recorded for the correct "bill date" in the billing system at the billing office. Among the disadvantages thereof, this approach is time consuming, requires multiple steps and the running of multiple programs and relies on visual comparison of data for verification.

In an alternative, preferred implementation of this embodiment of the invention, an automated procedure is used wherein, each night (for example), a computer at the billing office connects, via modem, to the event capture system of each billing client and downloads, in a compressed and encrypted form, the updated treatment information (i.e., event capture data). The next day (e.g., in the morning), at the billing office, the billing manager simply runs a milestone validation program which determines the weekly treatment milestones reached for each client and automatically determines if the corresponding weekly treatment charge (which is, again, identified by a specific code) was properly recorded in the billing system on the correct bill date for each milestone reached. This automated data validation between the two systems is now possible because a daily copy of each client's event capture data is available locally within the same computer network as the client's billing data stored. It will be appreciated that this approach is quick and easy as compared with the first approach described above, with only one program being used and with verification being provided by electronic comparison of data.

It will be appreciated from the foregoing that one of the key aspects of the basic billing method of the invention is that the method provides documentation-based billing, i.e., the system provides for billing for only charges that are documented, and thus that some kind of documentation is required to support each charge. Further, the "real-time" billing (i.e., billing based on the actual posting of charges into the system and sending invoices) provided by the invention is superior to "batch" billing in that the latter causes delays in posting and, therefore, in receipt of payments. The delay in posting charges is also disadvantageous because of the timely filing requirements imposed by insurance companies. It will be appreciated that such posting delays make it difficult to meet time deadlines when charges are contested.

A basic goal of any billing system is to get the billing done right the first time. It is expensive to work on payment denials from insurance companies and thus there is a premium place on getting it right the first time even if this requires extra care. Assistance is required to perform real-time, document based billing in that it is not efficient to randomly pull patient charts and look for billable charges. As indicated above, for the physician, the largest chargeable procedure is the weekly treatment charge and this charge is only billable once for every five treatments given to a patient. Thus, statistically, random chart pulls would result in 80% (four-fifths) of the charts pulled not having billable charges. The milestone approach of the present invention increases billing efficiency because every chart pulled due to a milestone contains at least the billable weekly treatment charge. It has been shown that the longer it takes to detect an error, the more difficult it is to correct the error and thus it is also important to facilitate prompt detection, and prompt correction, of errors.

The billing method of a preferred embodiment of the invention uses the milestone report as a queuing mechanism but also relies on the billing personnel to review associated patient documentation to find all other additional charges and to verify that the weekly treatment charge is itself correct and assists in the process. (it would be possible for a therapist to erroneously indicate to the charge capture system that a treatment was given; the patient chart is the final arbiter.) It will be appreciated that there are many other charges not encompassed by the weekly billing charge, but that the weekly treatment charge is advantageous as a sentinel or queuing mechanism for billing of other charges. As indicated above, these other charges (which include those mentioned in the introductory portion of this application) are detected manually by the billing personnel.

It will be understood from the foregoing that by centering the capture event at the point of treatment, the invention avoids the pressure that can be generated where billing is initiated when a patient is scheduled for treatment. In other words, rather than focusing on the scheduling of treatments (e.g., where scanning of a patient identifier in connection with the billing process would take place in the reception area rather than the treatment room) and thus producing a situation where a question would be raised by the billing system when there is no actual treatment, the focus is on the point of treatment where the treating physician has already decided that a particular treatment is appropriate.

Although the invention has been described above in relation to preferred embodiments thereof, it will be understood by those skilled in the art that variations and modifications can be effected in these preferred embodiments without departing from the scope and spirit of the invention.

What is claimed:

1. A billing method for billing for medical treatments, said method comprising:

capturing a treatment event by electronically scanning, at a time of the treatment event, a machine readable patient identifier carried by a patient treatment chart having entered thereon a prescribed treatment;

entering the captured treatment event into a computerized billing system along with the corresponding patient identifier;

using the patient treatment chart to validate charges entered into the billing system;

collecting all treatment events that are entered into the billing system for a specific patient identifier; and generating an invoice for all of the collected treatment events entered into the billing system for the specific patient identifier.

2. A method as claimed in claim 1 wherein said patient treatment chart contains a prescribed schedule of treatments for the patient.

3. A method as claimed in claim 2 further comprising providing an indication whether or not a specific treatment of the prescribed schedule of treatments has been carried out.

4. A method as claimed in claim 3 wherein a dialog box is presented to a user on a monitor located at a site at which the treatment event takes place, said dialog box presenting choices corresponding to (i) full treatment, (ii) partial treatment and (iii) no treatment and wherein the user checks an appropriate box to indicate to the billing system the treatment, if any, that was performed.

5. A method as claimed in claim 1 wherein the treatment event is entered into the treatment chart at the time the treatment takes place.

6. A method as claimed in claim 1 wherein the patient treatment chart is used to verify that appropriate documentation exists for all charges entered into the billing system.

7. A method as claimed in claim 1 wherein a milestone billing report is generated after a predetermined number of said treatment events is captured and wherein generation of an invoice by the billing system takes place responsive to the generation of the milestone report.

8. A method as claimed in claim 7 wherein the billing system designates every fifth treatment event as a milestone for triggering generation of said milestone billing report.

9. A method as claimed in claim 8 wherein the milestone billing report includes a patient name, milestone information and bill date for a given milestone, said bill date being the date of the first treatment event of the treatment events leading up to the milestone.

10. A method as claimed in claim 9 wherein, when a full course of treatment for the patient is completed and the number of leftover unbilled treatments is not divisible by five, the billing system, in billing for the leftover treatments when there are at least three treatments, treats the leftover treatments as a further milestone and assigns as a bill date for the milestone the date of the first of the leftover treatments.

11. A method as claimed in claim 8 wherein the billing system enables a user to log on to check whether said milestones are being properly reported.

12. A method as claimed in claim 11 wherein a check is made by the billing system when a milestone is generated to check for at least one of the following errors: (i) items on the patient chart are not billed out and (ii) a prescribed treatment schedule is not entered into the chart.

13. A method as claimed in claim 1 wherein the billing system provides that, in generating the invoice, nothing can be billed for that is not entered into the patient treatment chart.

14. A method as claimed in claim 1, wherein a characteristic audio signal, previously assigned to the patient and unique to the patient, is generated when there is a match between the patient identifier carried by the treatment chart and a stored patient identifier.

15. A billing method for billing for medical treatments administered to a patient, said method comprising:

capturing an independent treatment event by electronically scanning, at a time of the independent treatment event, a machine readable patient identifier for identifying the patient;

entering, at the time of the treatment event, data with respect to the treatment event, and other billable items, into a patient treatment chart associated with a specific patient identifier;

monitoring the treatment events captured for each specific patient identifier and, when the number of treatment events for a specific patient identifier reaches a predetermined number, selecting the patient treatment chart associated with the specific patient identifier; and when the treatment chart is selected, generating an invoice identified by the patient identifier based on the patient treatment chart.

16. A method as claimed in claim 15 wherein said machine readable identifier is carried by the patient treatment chart and said patient treatment chart has entered thereon a prescribed schedule of treatment events.

17. A method as claimed in claim 15 further comprising electronically scanning a corresponding machine readable patient identifier associated with an element employed in connection with the treatment event.

18. A method as claimed in claim 17 wherein said element comprises a port film.

19. A method as claimed in claim 17 wherein said element comprises a diode.

20. A method as claimed in claim 15 further comprising providing an indication whether or not a specific treatment of the prescribed schedule of treatments has been carried out.

21. A method as claimed in claim 20 wherein a dialog box is presented to a user on a monitor located at the site at which the treatment event takes place, said dialog box presenting choices corresponding to (i) full treatment, (ii) partial treatment and (iii) no treatment and wherein the user checks the appropriate box to indicate to the billing system the treatment, if any, that was performed.

22. A method as claimed in claim 15 wherein said predetermined number is five and a milestone billing report is generated each time the number of treatment events reaches a milestone of a fifth successive treatment in a series of treatments of a patient.

23. A method as claimed in claim 22 wherein the milestone billing report includes a patient name, milestone information and bill date for a given milestone, said bill date being designated as the date of the first treatment event of the treatment events leading up to the milestone.

24. A method as claimed in claim 22 wherein, when a full course of treatment for the patient is completed and the number of leftover unbilled treatments is not divisible by five, the billing system, in billing for the leftover treatments, treats the leftover treatments as a further milestone should there be at least three treatments and assigns as the bill date the date of the first of the leftover treatments.

25. A method as claimed in claim 24 wherein the billing system enables a user to log on to check whether said milestones are being properly reported.

26. A method as claimed in claim 22 wherein said treatment events are captured at a plurality of different treatment sites and a computerized billing system at a central billing office is used to determine the number of milestones reached for each treatment site during a preselected billing period and automatically checking if the corresponding charge for said period is recorded on the billing system on the correct bill date for each milestone reached.

27. A method as claimed in claim 15, wherein a characteristic audio signal, previously assigned to the patient and unique to the patient, is generated when there is a match between the patient identifier being scanned and a stored patient identifier.

28. A method of facilitating billing for medical treatment services involving treatment of a patient wherein a patient treatment chart is used in conjunction with the treatment of the patient, said method comprising the steps of:

logging onto a computerized billing system when the patient treatment chart is located at a predetermined location in a treatment facility; and generating a billing alert in response to said logging on step so as to ensure patient treatment provided at said location will be billed out.

29. A method as claimed in claim 28 wherein said logging on step comprises logging on responsive to use of a scanning device located at said predetermined location to scan a patient identifier on said patient treatment chart.

30. A method as claimed in claim 1 further comprising electronically scanning a corresponding machine readable patient identifier associated with an element employed in connection with the treatment event.

31. A method as claimed in claim 30 wherein the patient treatment chart carries said machine readable patient identifier and is scanned prior to scanning of said element, and wherein scanning of said element is delayed a predetermined period after scanning of said patient treatment chart.

32. A method as claimed in claim 30 wherein the patient treatment chart carries said machine readable patient identifier, and at least said patient treatment chart must be scanned prior to scanning of said element.

33. A method as claimed in claim 32 wherein a patient photograph also carries said patient identifier and said patient photograph must also be scanned prior to scanning said element.

34. A method as claimed in claim 1 further comprising producing a checklist for potentially billable standard numeric codes identifying physician services, based on matching thereto of a further standard code assigned in accordance with a treating physician's diagnosis, and using the checklist for placing documented but unfiled results in the record.

35. A method as claimed in claim 1 wherein the patient treatment chart includes a proposed treatment plan for the patient, and the method further comprises scanning of the patient treatment chart to provide an indication of potentially billable items associated with the proposed treatment plan.

36. A method as claimed in claim 1 wherein the captured event and corresponding patient identifier are entered into a workstation monitor of the computerized billing system and the method further comprises presenting sidebar boxes on the workstation monitor which list potentially billable items.

37. A method as claimed in claim 1 wherein the centralized computerized billing system receives billing information from at least one event capture system of each of a plurality of different billing sources.

38. A method as claimed in claim 37 wherein, on a given day, the centralized system receives, by modem, updated billing information from each said event capture system and downloads, in a compressed and encrypted form, the updated billing information, and wherein, on the following day, the computerized billing system automatically determines whether a predetermined number of treatment events has been reached for any of the patient identifiers and, if so, determines, for each, whether a corresponding weekly treatment charge has been correctly entered into the billing system on a correct bill date based on the updated billing information and previously stored billing information.

* * * * *